United States Patent [19]
Hughes et al.

[11] Patent Number: 5,199,299
[45] Date of Patent: Apr. 6, 1993

[54] ULTRASONIC UNIPOLAR PULSE/ECHO INSTRUMENT

[75] Inventors: Michael S. Hughes; David K. Hsu; Donald O. Thompson; Samuel J. Wormley, all of Ames, Iowa

[73] Assignee: Iowa State University Research Foundation, Inc., Ames, Iowa

[21] Appl. No.: 667,437

[22] Filed: Mar. 11, 1991

[51] Int. Cl.⁵ .................. H04B 1/02; G01N 29/10; G01N 29/24
[52] U.S. Cl. .................... 73/610; 367/137; 367/903; 73/629
[58] Field of Search ............... 73/609, 610, 620, 629, 73/632, 642, 612, 614; 367/135, 137, 903; 310/314, 316, 317, 318, 319

[56] References Cited

U.S. PATENT DOCUMENTS

| | | | |
|---|---|---|---|
| 4,193,306 | 3/1980 | Flaherty et al. | 73/629 |
| 4,222,113 | 9/1980 | Hansen | 367/87 |
| 4,234,939 | 11/1980 | Grall | 367/87 |
| 4,442,512 | 4/1984 | Kodera et al. | 367/87 |
| 4,534,221 | 8/1985 | Fife et al. | 73/626 |
| 4,563,899 | 1/1986 | Nakamura | 73/632 |
| 4,731,762 | 3/1988 | Hanks | 367/108 |
| 4,799,177 | 1/1989 | Sarr | 364/563 |
| 4,817,066 | 3/1989 | Takasugi et al. | 367/137 |
| 4,835,519 | 5/1989 | Suzaki et al. | 73/632 |
| 4,850,226 | 7/1989 | Allen, Jr. et al. | 73/610 |

Primary Examiner—Hezron E. Williams
Assistant Examiner—Rose M. Finley
Attorney, Agent, or Firm—Zarley, McKee, Thomte, Voorhees & Sease

[57] ABSTRACT

An ultrasonic unipolar pulse/echo instrument uses active switches and a timing and drive circuitry to control electrical energy to a transducer, the discharging of the transducer, and the opening of an electrical pathway to the receiving circuitry for the returning echoes. The active switches utilize MOSFET devices along with decoupling circuitry to insure the preservation of the unipolar nature of the pulses, insure fast transition times, and maintain broad band width and time resolution. A housing contains the various circuitry and switches and allows connection to a power supply and a movable ultrasonic transducer. The circuitry maintains low impedance input to the transducer during transmitting cycles, and high impedance between the transducer and the receiving circuit during receive cycles to maintain the unipolar pulse shape. A unipolar pulse is valuable for nondestructive evaluation, a prime use for the present instrument.

21 Claims, 7 Drawing Sheets

ULTRASONIC UNIPOLAR PULSE/ECHO INSTRUMENT

GOVERNMENT PATENT RIGHTS

This invention was made with Government support at least in part under contract #W-7405-ENG-182 awarded by the Department of Energy. The Government may have certain rights in the invention.

BACKGROUND OF THE INVENTION

1. Field of the Invention

The present invention relates to a means and method for transmitting and receiving ultrasonic energy, and in particular, one which allows the use of a single ultrasonic transducer in a pulse/echo mode to generate and receive unipolar ultrasonic pulses over a wide frequency bandwidth.

2. Problems in the Art

Ultrasonic interrogation is a widely used and promising technique of nondestructive evaluation. Nondestructive evaluation allows analysis of the interior of materials or structures without physically opening up or breaking into the interior. The advantages of this are obvious.

It has been firmly established that ultrasound can be propagated into a material and that its returning echoes will contain information about the structure of the interior of the material. For example, ultrasonic waves directed into a solid, generally homogeneous material, should result in reflected echoes which are unperturbed. If, however, the material contain cracks, voids, discontinuities, or such things, the reflected echoes should give an indication of the existence of these types of things. Major problems exist, however, in obtaining reliable and pertinent information from the echoes, and interpreting the echoes.

A co-pending, co-owned application filed Feb. 8, 1990, by inventors Thompson and Hsu, entitled MEANS AND METHOD OF TRANSMITTING AND RECEIVING BROADBAND, UNIPOLAR ULTRASONIC PULSES FOR ULTRASONIC INSPECTION, (which is a continuation application from Ser. No. 181,094 filed Apr. 13, 1988) discusses in some detail the differences in the types of ultrasonic pulses that are used in ultrasonic nondestructive evaluation. It also discusses why what are called "unipolar pulses" are believed to be better than "bipolar pulses" in many cases of ultrasonic non-destructive inspection and evaluation.

The above referenced application discusses the significant problems encountered in generating and receiving unipolar ultrasonic pulses. It discloses one structure and method for doing so. Circuitry was used incorporating two what will be called "passive" switching elements to "switch" the circuitry between the transmit (or pulse) and the receive (or echo) portions of each cycle. These passive switches also ensure appropriate impedances in the circuit to maintain the unipolar nature of the ultrasonic pulses from their generation to their reception.

It has been found that there is room for improvement with regard to this design. For example, it required utilization of and connection to a discrete square wave generator device, which in actuality itself contained a switch which was needed to maintain the unipolar nature of the pulses. It would be advantageous to be able to incorporate the square wave generator into the circuitry of an instrument to avoid the necessity of a separate square wave generator.

Additionally, there is a need for a unitary instrument that has a quicker transition time between transmit and receive states and maintains or improves upon the excellent bandwidth and time resolution of the co-pending application.

While the device described in the above mentioned application does present a viable way of generating and receiving unipolar ultrasonic pulses, there is a need in the art for improvement of the procedure and instrument used for the procedure. It is therefore a primary object of the present invention to provide an ultrasonic unipolar pulse/echo instrument and method which improves over or solves the problems and deficiencies in the art.

Another object of the present invention is to provide an instrument and method as above described which maintains the unipolar nature of the ultrasonic pulses in both the transmit (pulse) and receive (echo) portions of each cycle.

A still further object of the present invention is to provide an instrument and method as above described which has an improved bandwidth without sacrificing time resolution.

A still further object of the present invention is to provide and instrument and method as above described which results in improved return echoes of the unipolar pulses.

A further object of the present invention is to provide an instrument and method which utilizes active switches to accomplish improved unipolar pulse/echo operation.

Another object of the present invention is to provide an instrument and method as above described which results in improved output voltage during transmission and fast transition between transmit and receive operations.

Another object of the present invention is to provide an instrument and method as above described which can be operated from a single unitary instrument.

Another object of the present invention is to provide an instrument and method as above described which is reliable, efficient, and economical.

These and other objects, features, and advantages of the present invention will become apparent with reference to the accompanying specification and claims.

SUMMARY OF THE INVENTION

The present invention relates to an instrument and method for transmitting and receiving ultrasonic pulses for nondestructive evaluation of materials. The invention represents an improvement over co-pending and co-owned U.S. Ser. No. 477,162, and parent application Ser. No. 181,094, now abandoned, referenced above and which are incorporated by reference with this disclosure.

The present invention utilizes a conventional ultrasonic transducer to transmit and receive ultrasonic pulses. The transducer operates in what is called a "pulse/echo" mode of both transmitting and receiving. The circuitry connected to the transducer therefore must time and control transmission and reception so that they do not overlap or conflict with one another, because they must be performed by the same transducer. At the same time, the present invention seeks to generate and maintain unipolar ultrasonic pulses. This requires that certain differences in impedances be set up in the circuitry at different times during the transmit and receive cycles.

The instrument contains within a housing a timing and drive circuit, several power supplies, a receive and amplify circuit, and three switch means. The instrument is connectable to a standard service alternating current power supply. The transducer element is contained with a holder which is connectable by coaxial connectors and coaxial cable to a coaxial connector on the instrument. The transducer can therefore be moved around to a considerable extent without having to move the instrument.

The power supplies convert the standard AC line voltage to desired direct current power supplies. One is a variable DC voltage supply that is used as the variable excitation voltage for charging the transducer. Another DC power supply is utilized by various components of the circuitry and is not variable.

The timing and drive circuitry controls the operation of the instrument. For example, it controls operation of a first switch means to allow the excitation voltage to charge the transducer. It then opens the first switch means and closes a second switch means which is connected to an extremely low impedance pathway. This discharges the transducer very quickly to produce the mechanical ultrasonic acoustic pulse. The third switch means opens and closes the pathway to the receiving and amplifying circuitry. This switch means closes after the ultrasonic pulse is transmitted so that the transducer can receive the reflected echo of the pulse, convert that mechanical energy into an electrical signal, and communicate that signal to the reception and amplifying circuitry where it can be prepared for output.

Each of the switch means is an "active" switch as compared to the "passive" switches utilized in the application incorporated by reference. The timing and drive circuitry gives the instructions to cause the actual switching elements to open or close, as compared to the diode configuration in the application incorporated by reference which served as passive switches depending on the particular electrical pathway.

DETAILED DESCRIPTION OF THE PREFERRED EMBODIMENT

In order to assist in an understanding of the invention, a preferred embodiment of the invention will now be described in detail. It is to be understood that this is only a preferred embodiment of the invention, and does not describe all the forms the invention can take.

In this description, reference will be taken to the drawings. Reference numerals will be used to indicate parts and locations in the drawings. The same reference numerals will be used for the same parts and locations in all of the drawings, unless otherwise indicated.

It is important to an understanding of the invention to understand the predecessor to this invention. As previously discussed, the application incorporated by reference discloses and claims a unipolar pulse/echo means and method. With reference to that application, it becomes apparent that the circuitry is designed with what are called "passive switches", which by their nature allow for the very quick cycling of the single ultrasonic transducer between a transmit mode and a receive mode. Likewise, the circuitry involved with the transducer must perform different functions during those cycles, and those passive switches operate to allow these functions while at the same time presenting the appropriate impedances in the circuitry to create and maintain ultrasonic pulses which are unipolar in nature.

Figure 1:
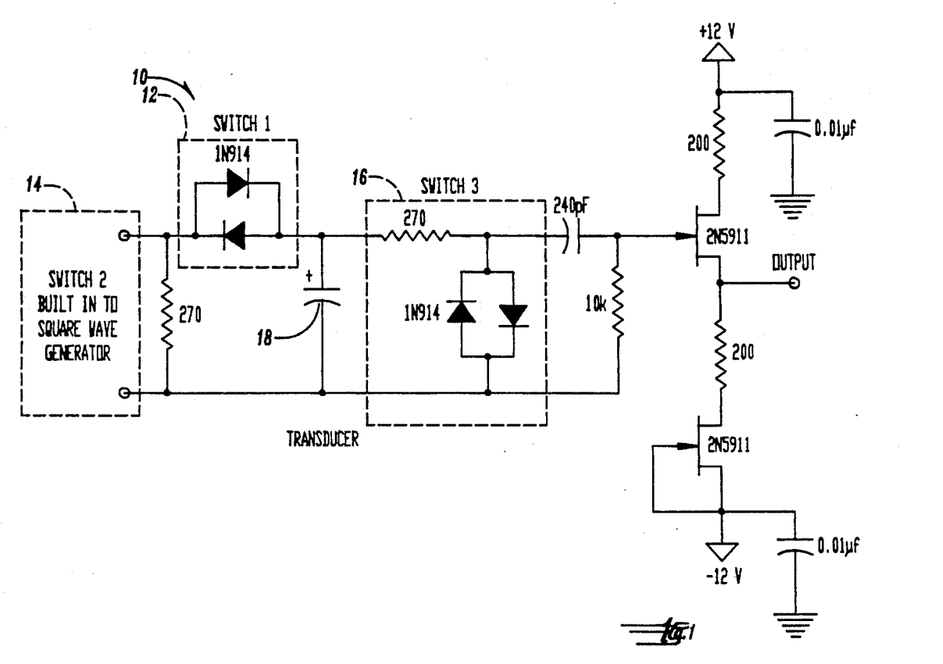
FIG. 1 is an electrical schematic of a passive-switched unipolar pulse/echo circuitry.

For comparison purposes to the present invention, FIG. 1 is a schematic representation of a circuit 10 representative of the unipolar pulse/echo circuit of co-pending and co-owned U.S. Ser. No. 477,162 and parent application Ser. No. 181,094. First, second, and third passive switches 12, 14, and 16 respectively, are indicated within dashed boxes. As can be immediately seen, the unique diode configurations in passive switch 1 (reference #12) and switch 3 (reference #16) can be seen.

It is to be understood that circuit 10 was designed specifically for use with a low output impedance commercial square wave generator. Circuit 10 could then be put into a package which could be directly connected to such a generator. It was determined that switch means 2 (reference #14) actually existed inside such square wave generator. A first, and significant difference with the present invention is that the square wave generator of the present invention is "built-in" to the circuitry, and no external square wave unit and hook ups are required.

Circuit 10 of FIG. 1 operates as follows. During each transmit portion of the pulse/echo of ultrasound from transducer 18, switch 1 (reference #12) is "closed" as the output of the square wave generator is high (about 50 volts). An electrical pathway therefore exists to transducer 18 so that it can be charged by permitting this high voltage to be applied to transducer 18.

In circuit 10, only one of the three switches is closed as any particular time. Therefore, during the transmit portion of the cycle, switch 12 is closed, whereas switches 2 and 3 are basically "open". For example, switch 3 is effectively open because any voltage above one diode drop (0.7 volts) is shorted out by the clipping diodes in that switch.

The next portion of the cycle involves closing switch 2 inside of the square wave generator which pulls down its output voltage in a very short time (10–20 nanoseconds or ns). The output of the square wave generator therefore quickly drops to 0. This causes transducer 18 to discharge electrical energy stored in it which produces a mechanical acoustic ultrasonic pulse which propagates away from transducer 18.

The immediate return echoes of the transmitted ultrasound are "received" by transducer 18. Just as electrical energy stored and discharged from transducer 18 produces a mechanical acoustical wave with certain properties, reflected mechanical acoustical waves that return into transducer 18 cause it to vibrate and produce an electrical signal. Such operation is well known by those of ordinary skill in the art. However, during this "receive" portion of the cycle, switch 1 is effectively open because the magnitude of the return echoes is almost always less than one diode drop in switch 1. This passive operation basically results in the electrical signals from transducer 18 being allowed to travel through the effectively "closed" switch 3 to receiving circuitry. The electrical signals caused by the return echoes effectively do not "see" the low impedance of the square wave generator, which are needed to drive the transducer which has a very small input impedance. This is discussed in detail in application Ser. No. 477,162. It was also pointed out that such an arrangement is an essential requirement for generation and reception of unipolar pulses. If this relationship did not exist, the return signal picked up by the transducer, having an extremely high output impedance, would be high-pass filtered by the low impedance elements of the square wave generator.

It can therefore be seen how the three "passive switches" of circuit 10 would "passively" cooperate to achieve the transmit/receive (pulse/echo) cycles while at the same time producing the unipolar pulses which are at the heart of such an invention. Such a circuit, however, proved to have some disadvantages and the need for improvements were recognized.

Therefore, the need was perceived for a total, unitary instrument which could more effectively produce pulse/echo operation of a conventional transducer while also generating maintaining, and receiving unipolar pulses. By referring to FIG. 2, a general block-form electrical schematic of circuit 20 according to the present invention is depicted. The primary differences from circuit 10 are as follows. First of all, circuit 20 requires a timing and drive circuit 22. This circuit 22 is basically the control center for operating three "active" switches 1, 2, and 3 (alternatively designated by reference nos. 24, 26, and 28 respectively). The need for connection to a separate square wave generator has been eliminated. A variable power supply 30 is incorporated into circuit 20. Additionally, a receiver circuit (32) which includes an amplification subcircuit is also present.

Figure 2:
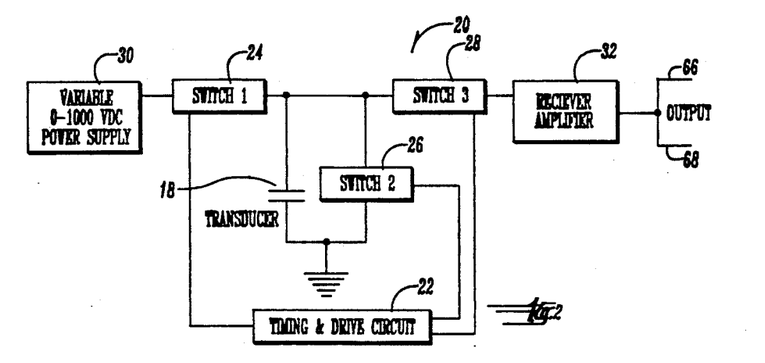
FIG. 2 is a diagrammatical representation of the active switch pulse/echo circuitry of the present invention.

Transducer 18 (again a conventional piezoelectric transducer in the preferred embodiment) is incorporated into the circuit so that switch 1 is between it and power supply 30. Switch 1 functions to close the electrical pathway and allow electrical power from power supply 30 to charge transducer 18 during one portion of each pulse/echo cycle.

Switch 2 is positioned between transducer 18 and the receiver circuit 32. Again, switch 2 closes, upon instruction of circuit 22, to discharge electrical energy from transducer 18 to generate the ultrasonic pulse.

Finally, switch 3 is connected between transducer 18 and the receiver circuit 32 and closes, upon instruction, circuit 22, during the portion of the cycle where the reflected ultrasound is captured and converted into an electrical signal by transducer 18, passing those signals to the receiver circuit 32.

FIG. 2 also shows timing and device circuit 22 is directly connected to each of switches 1, 2, and 3. As will be discussed later, circuit 22 controls the opening and closing of each of these switches. As is easily understood, each of the switches therefore is an "active switch"; opening and closing according to external instruction (by circuit 22), as opposed to the "passive" nature of the switching described with respect to circuit 10.

Figure 3:
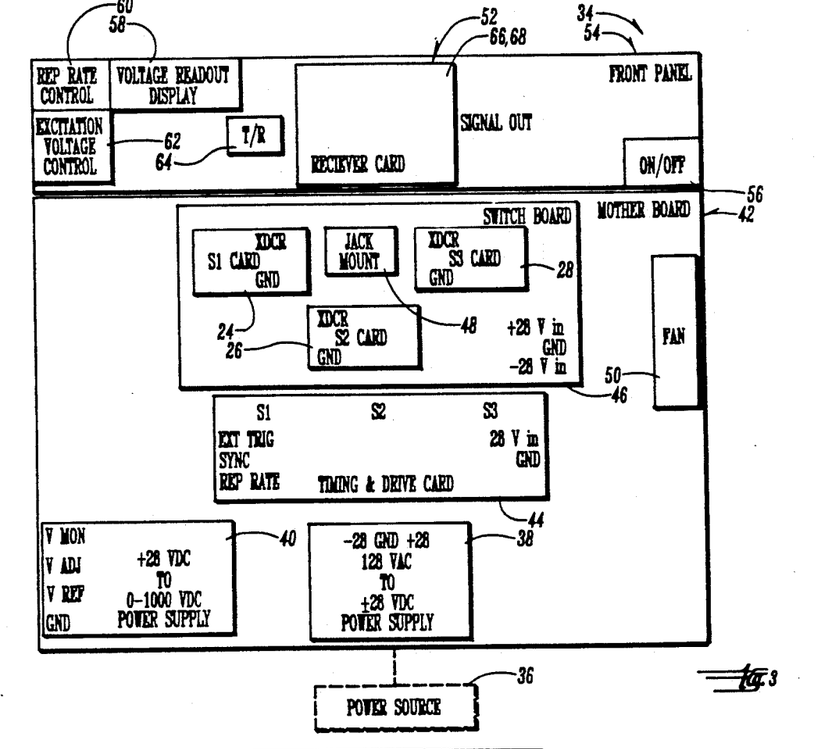
FIG. 3 is a block diagram of a preferred embodiment of the present invention depicting circuit cards or boards and elements for such a unipolar pulse/echo instrument.

FIG. 3 is a diagrammatic block layout of an instrument 34 according to the present invention. It is to be understood, that this is only one configuration the invention could take and is for illustrative purposes only.

Instrument 34 is connectable to a standard 128 VAC (volts/alternating current) external power supply (36). Internally, a first power supply 38 converts the line voltage (AC) to plus and minus 28 VDC (volts/direct current). A second power supply 40 converts plus 28 VDC to a 0-1,000 VDC variable power supply.

Both power supplies 38 and 40 are contained on the printed circuit boards which in turn are fastenable to a mother board 42, all such as is well known within the art.

A timing and drive printed circuit card 44 contains the timing and drive circuit 22. It is connectable to first power supply 38 and operates off of 28 VDC.

What will be called a switch board 46 contains separate printed circuit boards for each of active switches 1, 2, and 3 (reference nos. 24, 26, and 28). Additionally, switch board 46 is connectable to the first power of supply 38 and utilizes plus or minus 28 VDC. Additionally, a jack mount 48 is included on switch board 46 to allow connection and communication such as will be described later.

A fan 50, which can operate from the first power of supply 38, is included on the mother board to provide cooling circulation of air into and out of instrument 34, such as well know in the art.

FIG. 3 also diagrammatically depicts a receiver card 52 which would contain the receiving and amplifying circuitry for instrument 34. The front panel 54 of instrument 34 can include an on-off switch 56, a voltage readout display 58, a repetition rate control 60, an excitation voltage control 62, as well as an input jack for cable to transducer 18 (see reference #64), and a signal-out jack 66 so that the received signal, amplified by receiver circuit 32, can be communicated to additional equipment.

The arrangement depicted in FIG. 3 therefore shows a unitary unipolar pulse/echo instrument containing all needed circuitry. Instrument 34 is easily manufacturable and serviceable by nature of the design of all subcircuits on the printed circuit cards or boards. As is well appreciated in the art, the actual physical layout of circuit boards in instrument 34 has been carefully designed for optimal circuit performance in light of the fact of the presence of high frequency circuits. In the preferred embodiment, this layout has done away with problems such as slow switching times and poor noise immunity, with the result being instrument 34 has a signal to noise (S/N) ratio at least 20 dB higher than commercial units.

Figure 4:
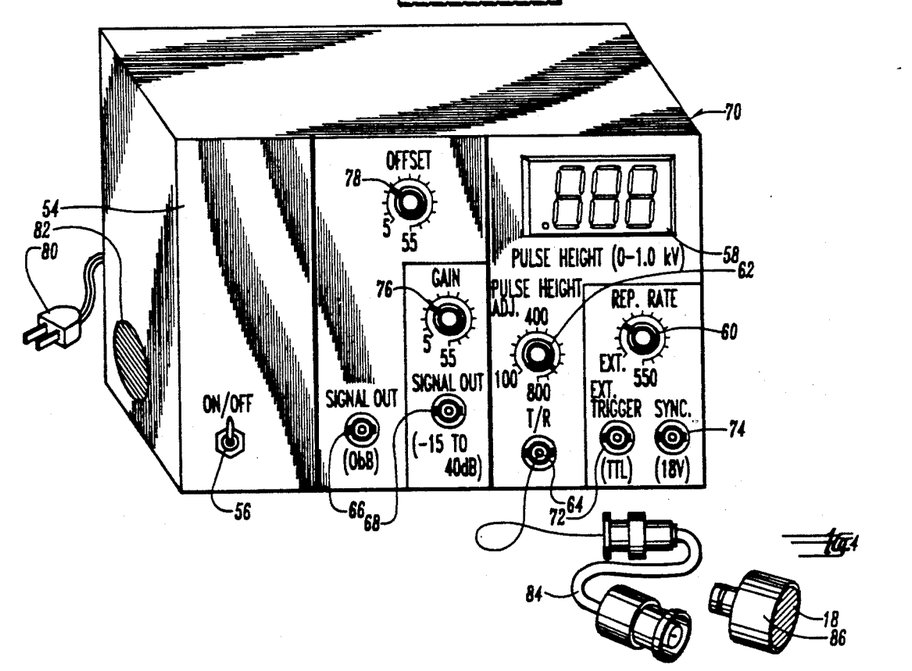
FIG. 4 is a perspective drawing of a preferred embodiment of the invention.

FIG. 4 depicts an example of how instrument 34 could look according to the preferred embodiment. A housing 70 would enclose all of the circuitry. Front panel 54 would contain display 58, on/off switch 56, repetition rate control 60, excitation voltage control 62, as well as input jack 64 and signal out jack 66. Also shown is an external trigger jack 72 and a sync jack 74.

A gain control 76 could also be incorporated to control the amount of amplification of receiver circuit 32 on receiver card 52. An offset control 78 could also be utilized.

FIG. 4 also shows electrical plug 80 used to access 128 VAC, a vent 82 in the side of housing 70 for air circulation of fan 50, as well as labeling of the various front panel items and calibration figures for the controls. It is furthermore noted that there are two signal-out jacks 66 and 68 in this particular embodiment. One is associated with gain control 76; the other is not.

FIG. 4 also depicts cable 84 which can be used to connect transducer holder 86 (containing transducer 18) to the "T/R" or input jack 64 on the front panel 54. Cable 84 can be of sufficient length to allow transducer 18 to be positioned and moved during operation of instrument 34.

The basic makeup of instrument 34 has now been described. Specifics of the circuitry, shown in block form in FIG. 3, will now be discussed.

FIG. 3 illsutrates that in the preferred embodiment, instrument 34 consists of a mother board 42, a switchboard 46, four printed circuit boards 24, 26, 28, and 48 on switchboard 46, three printed circuit boards 38, 40, and 44 directly on mother board 42, a printed circuit board 52 attached to front panel 54, and then readouts, switches, controls, and a fan. This is all contained within or on housing 70. Instrument 34 also contains 10 to 1,000 VDC electrical power supply, and two 28 VDC electrical power supplies.

Below will be individual descriptions of pertinent portions of the printed circuit boards corresponding to those shown in FIG. 3, as well as how they function within the system.

Figure 5:
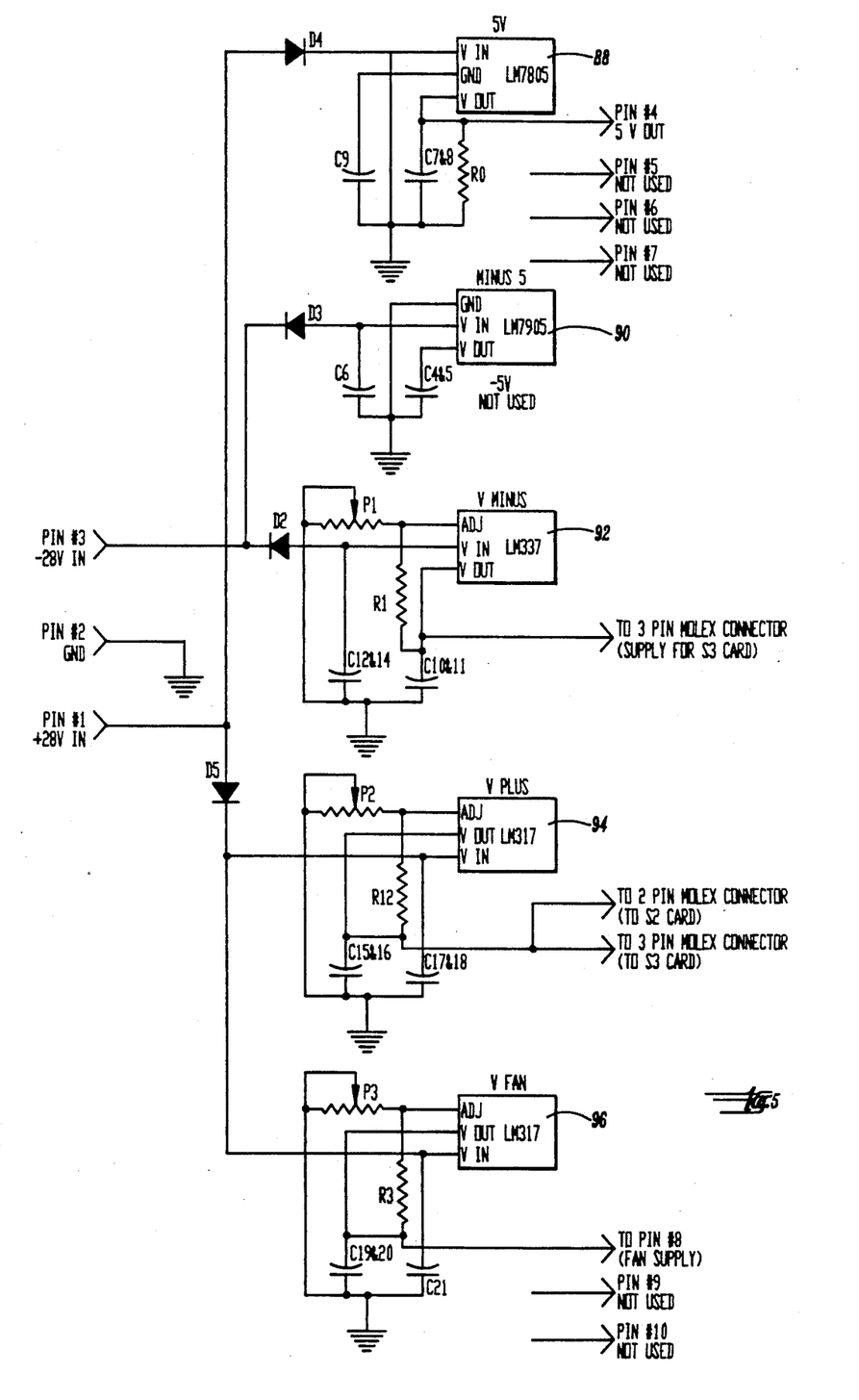
FIG. 5 is an electrical schematic of a portion of the power supply according to the preferred embodiment of the present invention.

FIG. 5 is an electrical schematic of power supply card or printed circuit board 38. The left side of the circuit provides inputs for plus and minus 28 VDC and a ground connection. The standard line 128 VAC is first converted to plus or minus VDC, and then introduced at this point.

As can be seen, voltage regulator components 88, 90, 92, 94, and 96 receive the plus or minus VDC and convert it into different output VDC usable by other parts of instrument 34. For example, component 88 along with diode D4 transform plus or minus VDC into 5 VDC which is available, for example, for miscellaneous digital equipment or components associated with the circuitry 34. Component 88 can be device identified by component part number LM7805 and, like all other parts in these schematics, is available under this number by a wide variety of electrical component manufacturers and/or suppliers.

Component 90 (which can be a device identified by LM7905) cooperates with diode D3 to produce an output of minus 5 VDC. Diode D3 is reversed from diode D4 and is connected to minus 28 VDC input. In the preferred embodiment, however, the minus 5 VDC is not used.

Component 92 (identified by #LM337) cooperates with diode D2, varistor P1, and the other shown components to take a minus 28 VDC and output an adjustable minus voltage DC (1.2-37 VDC). As can be seen, the output is used as a supply for card of printed circuit board 28 which contains active switch 3. As is further shown, connection can be made to a 3 pin molex connector, such as is well known in the art.

Component 94 (LM317) utilizes diode D5 and varistor P2 to convert a plus 28 VDC into a variable output positive voltage DC (1.2 to 37 VDC). This voltage is available through the indicated molex connectors to cards 26 and 28, containing active switches 2 and 3.

Finally, component 96 (also LM317) cooperates with diode D5 and varistor P3 to create a variable output voltage of a positive nature to fan 50.

Figure 6:
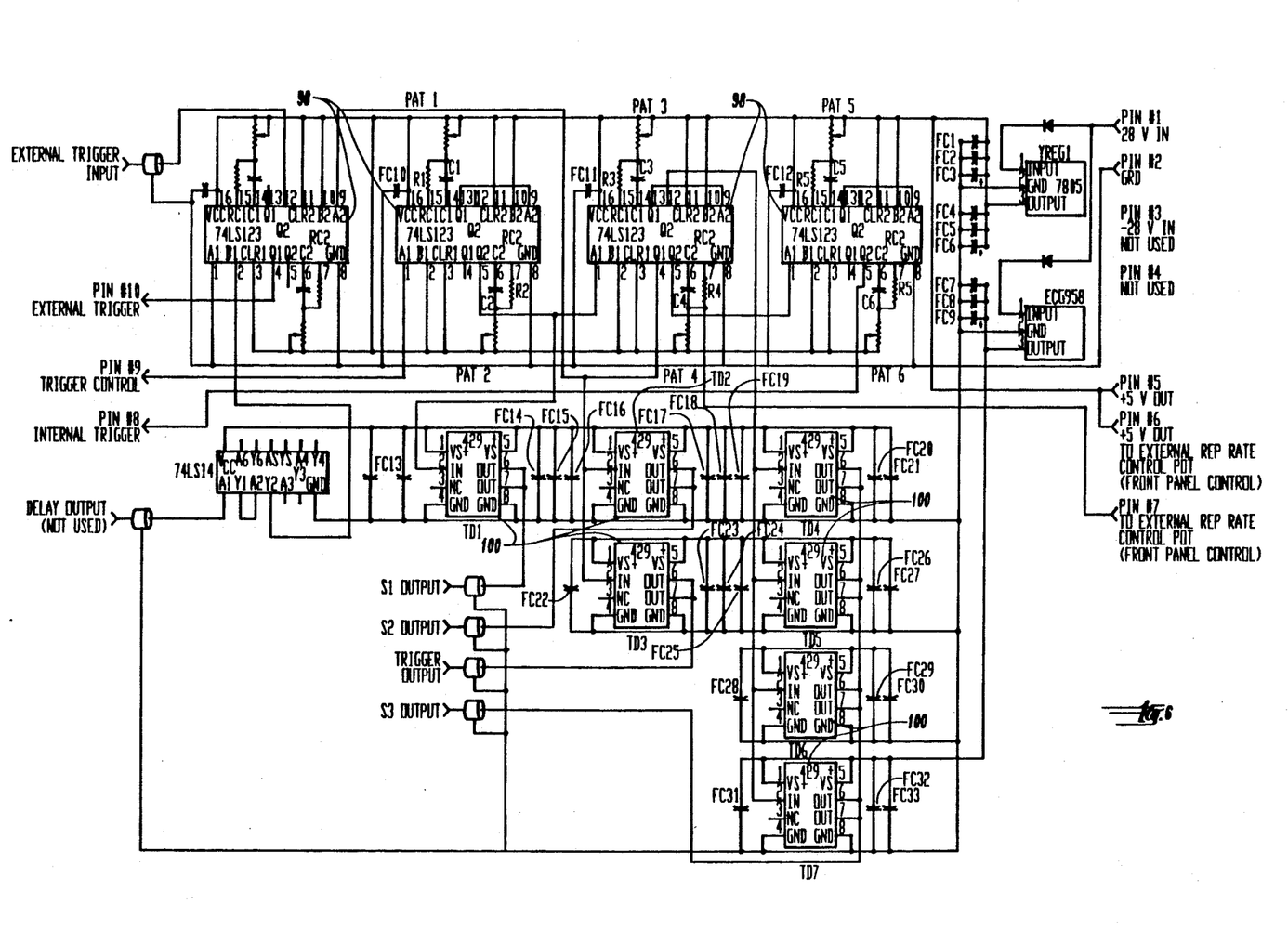
FIG. 6 is an electrical schematic of the timing and drive card shown in FIG. 3.

FIG. 6 is an electrical schematic of timing and drive card or printed circuit board 44. The circuitry is fairly conventional. Four 74LS123 (or alternatively 7HC123) dual one shot trigger devices 98 (IC-TTL Low Power Schottky, Dual Retriggerable Monostable Multivibrators) are powered by regulated voltage through device 7805, which in turn is connected +28VDC from the appropriate power supply in instrument 34. The dual one shots cyclically self-trigger timing pulses which are output to 7TSC429CPA power MOSFET drivers 100 (available from Teledyne).

It can also be seen that the dual one shots utilize plus 5 volts DC and are connected to the repetition rate control potentiometer 60 on front panel 54 of instrument 34 which serves as a manual control for the rate of timing pulses.

The MOSFET drivers 100 in turn are connectable through outputs from card 44 to cards 24, 26, and 28, which contain active switches 1, 2, and 3. As will be further discussed, each of the active switches 1, 2, and 3 contain power MOSFETs which are used in a switching capacity. The MOSFET drivers 100 drive the gate junctions of the MOSFETs in switches 1, 2, and 3.

It is to be understood that in timing and drive card 44, ground plane construction, such as well known in the art, is required to maintain extremely fast pulse transition times and to enhance noise immunity of the circuit.

Figure 7:
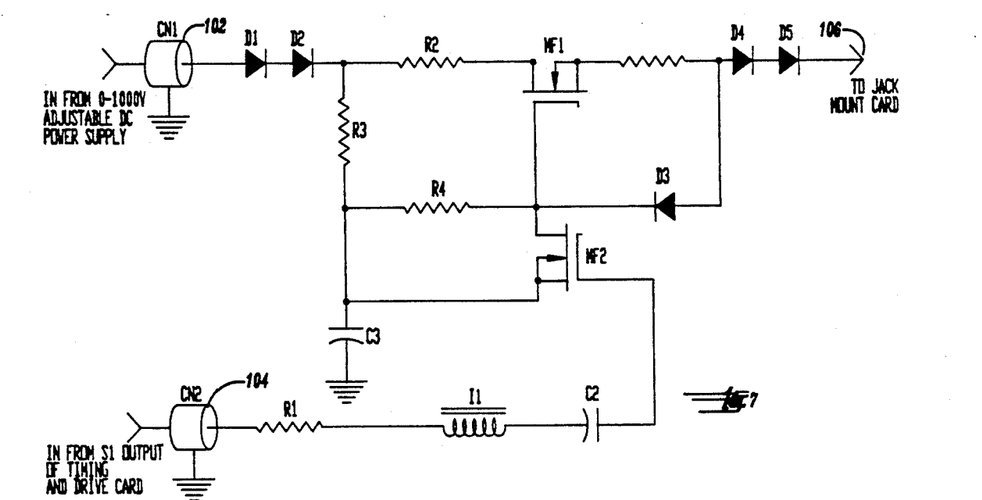
FIG. 7 is an electrical schematic of the S1 card of FIG. 3, which represents a first switching means of the invention.

FIG. 7 depicts the electrical schematic of the preferred embodiment of card 24 containing active switch 1. Coaxial connector 102 is in electrical communication from the 0-1,000 VDC power supply 40. Coaxial connector 104 is in electrical communication with the S1 output of timing and drive card 44. Each of these inputs are referenced to a separate ground other than the ground plane for the rest of the card. These separated grounds are connected together at the source of the power MOSFET in card 26 by utilizing jack mount card 48. Such an arrangement is essential to eliminate ground loops which will degrade the switching time by two orders of magnitude. It is to be understood that the same is true for cards 26 and 28.

As previously discussed, card 24, containing active switch 1, controls connection of the high voltage DC power supply to piezoelectric transducer element 18. When a timing signal from timing and drive card 22 is received through connector 104, gate voltage to power MOSFET MF2 opens an electrical path to fire the gate of power MOSFET MF1, in turn opening the electrical pathway from the 0-1,000 VDC input to output 106 which goes to jack mount card 48, and in turn to transducer 18 to charge it in preparation for transmission of an ultrasonic acoustic wave.

It is to be understood that the section of the circuit comprised of MF1, MF2, resistors R2-R5, and diode D3 is based on a Siemann's application as is known in the art. The additional elements, namely diodes D1-D5, and the band pass filter comprised of resistor R1, inductor I1, and capacitor C2, are a novel configuration required of this active switch to maintain the unipolar nature of the pulse and echo created by the circuit.

These latter elements basically "decouple" the return echoes from the low impedance path to ground, which would otherwise be available through the huge parasitic capacitance in the gate-source junction of MF2, or the parasitic drain-source capacitance in MF1. Similar decoupling is required in active switches 2 and 3. Such decoupling maintains the broad band unipolar pulse/echo ability of instrument 34.

Figure 8:
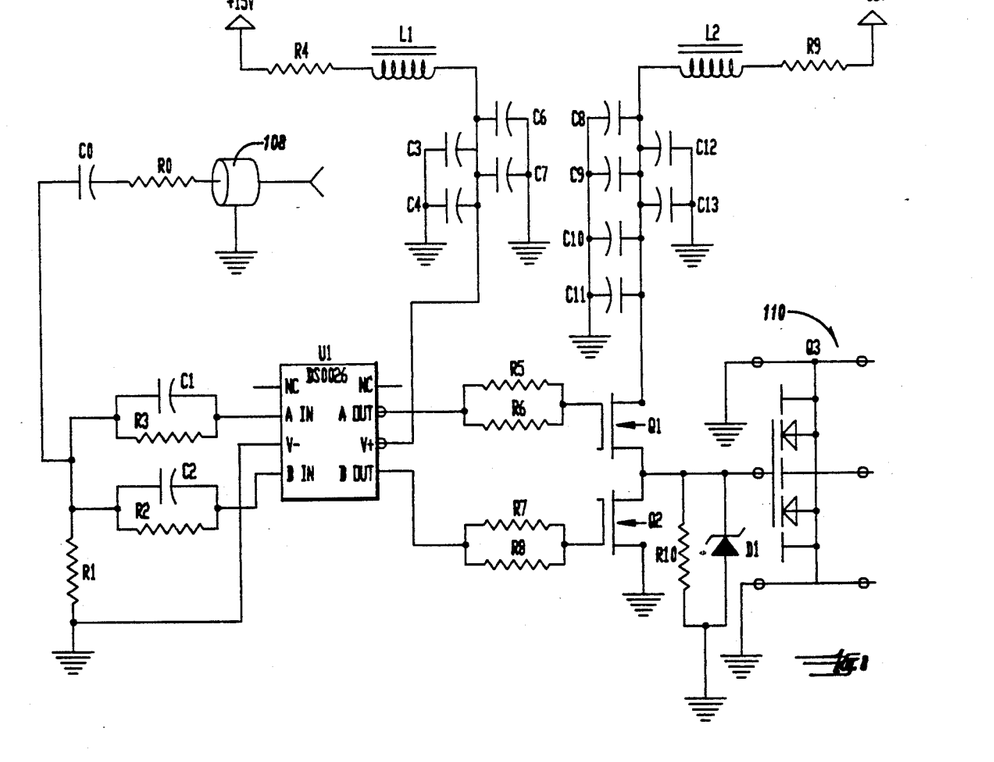
FIG. 8 is an electrical schematic of the S2 card or second switching means of FIG. 3.

FIG. 8 is the electrical schematic for circuit card 26 containing active switch 2. Coaxial connector 108 provides connection to the S2 output from timing and drive circuit 22. It again has a separate ground as previously explained. Device U1 (product #DS0026) is designed to take the timing pulses and distribute them to power MOSFET's Q1 and Q2. Transistor Q3 is connected at connection 110 to transducer 18.

Active switch 2 (card 26) rapidly drains stored charge built up on piezoelectric element 18 while switch 1 (card 24) is closed. When switch 1 is opened by a pulse from timing drive card 22, switch 2 closes providing an extremely low impedance path for a charge on the piezoelectric transducer element 18. This circuit can be obtained from Directed Energies Corporation. Resistor RO and capacitor CO were added to perform the decoupling of low frequency elements of return ultrasonic pulses to ground through the gate drive circuitry.

Figure 9:
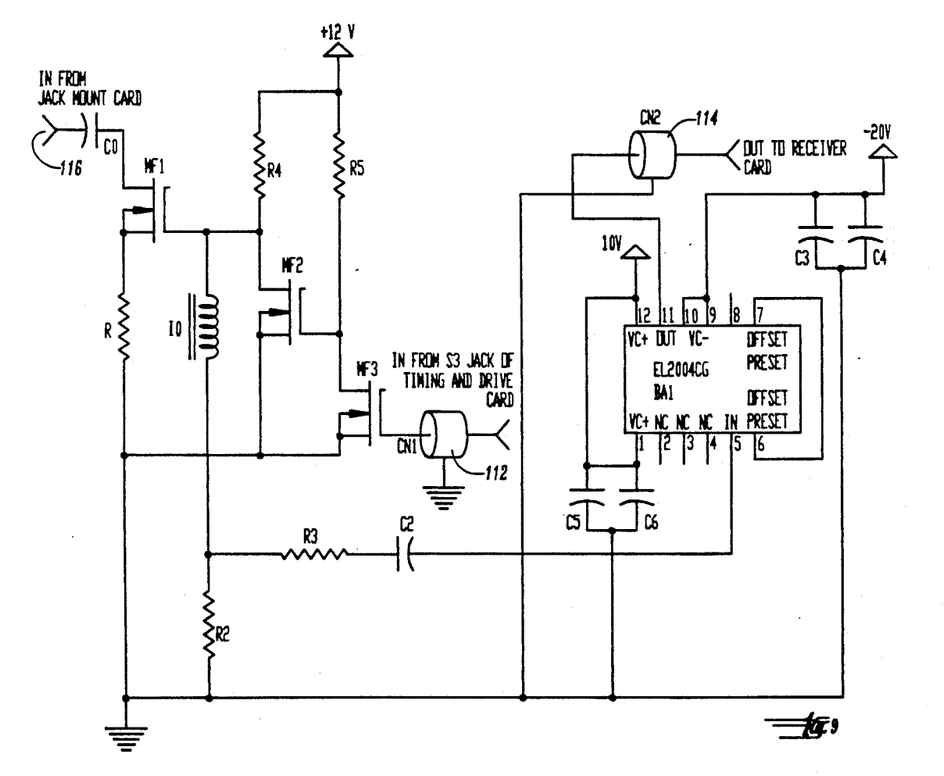
FIG. 9 is an electrical schematic of the S3 card or third switching means of FIG. 3.

FIG. 9 is an electrical schematic of card 28 containing active switch 3. An input 116 exists from jack mount card 48. Three power MOSFETs MF1, MF2, and MF3 are used in this circuit. Additionally, electrical device EL2004CG BA1 is utilized. A coaxial connector 112 provides electrical communication from the S3 output of timing and drive card 22. Coaxial connector 114 provides an output to receiver circuit and card 32.

The connection from the jack mount card 48 pertains to the ground plane connections and separate grounds discussed earlier with regard to card S1 (reference #24).

Card 28, shown in FIG. 9, allows instrument 34 to receive the returning ultrasonic echoes picked up by transducer 18, as well as provides current amplification required to drive long cables and gain block circuitry in the final output stages of instrument 34.

The configuration of the circuit of card 28 is such that it withstands the application up to 1,000 VDC to its input without damage. To overcome this problem, the invention utilizes a 1,000 volt power MOSFET.

As previously explained, a large parasitic capacitance exists in the drain-gate junction of each power MOSFET. As previously described, this presents substantial difficulties to the provision of a successful unipolar pulse/echo design.

In the other circuit cards, decoupling elements were introduced to solve the problem. In card 28, however, the circuitry is constructed to actually utilize the parasitic junction capacitance to the advantage of the circuit.

The circuit of card 28 couples return echoes into a buffer current amplifier (device EL2004CG BA1) with a limited voltage input range (plus or minus 20 volts). At the same time, the circuit protects the inputs of the amplifier from voltages up to 1,000 VDC, which may be used in exciting the transducer 18. This protection arises as a result of a characteristics of the drain/source junction of the power MOSFET which is fabricated to stand off voltages up to its rated specification (1,000 volts). It is important to hold the gate of this MOSFET (MF1) at ground during the time the 1,000 volt excitation is applied to the transducer element 18. Otherwise the gate junction will float up to the applied excitation voltage and destroy the buffer amplifier. It has been found that this type of coupling scheme passes the return echoes without measurable attenuation or distortion.

Moreover, the return echoes can be superposed on a nearly flat baseline. This is essential and very advantageous if the return echoes are to be amplified by up to 40 dB, because the presence of even a 20 mv/$\mu$s slope in the baseline of the unamplified return echoes will result in a 2v/$\mu$s slope in the baseline of the amplified return echoes. The presence of such a rapidly varying baseline will obscure the location and shape of return echoes. Even if the echoes can be identified in such a rf (radio frequency) trace, their subsequent analysis will be made much more difficult by the presence of the baseline.

Card 28, with active switch 3, therefore basically works as follows. After transmission of the ultrasonic pulse, the return echoes, captured by the piezoelectric transducer element 18 and converted into electrical signals, are channeled through a closed active switch 3 without attenuation or distortion, to the receiving circuit on card 32 where they are maintained and amplified. Pulses are maintained in their unipolar form and can then be output to an external device for viewing, analysis, or storage.

Figure 10:
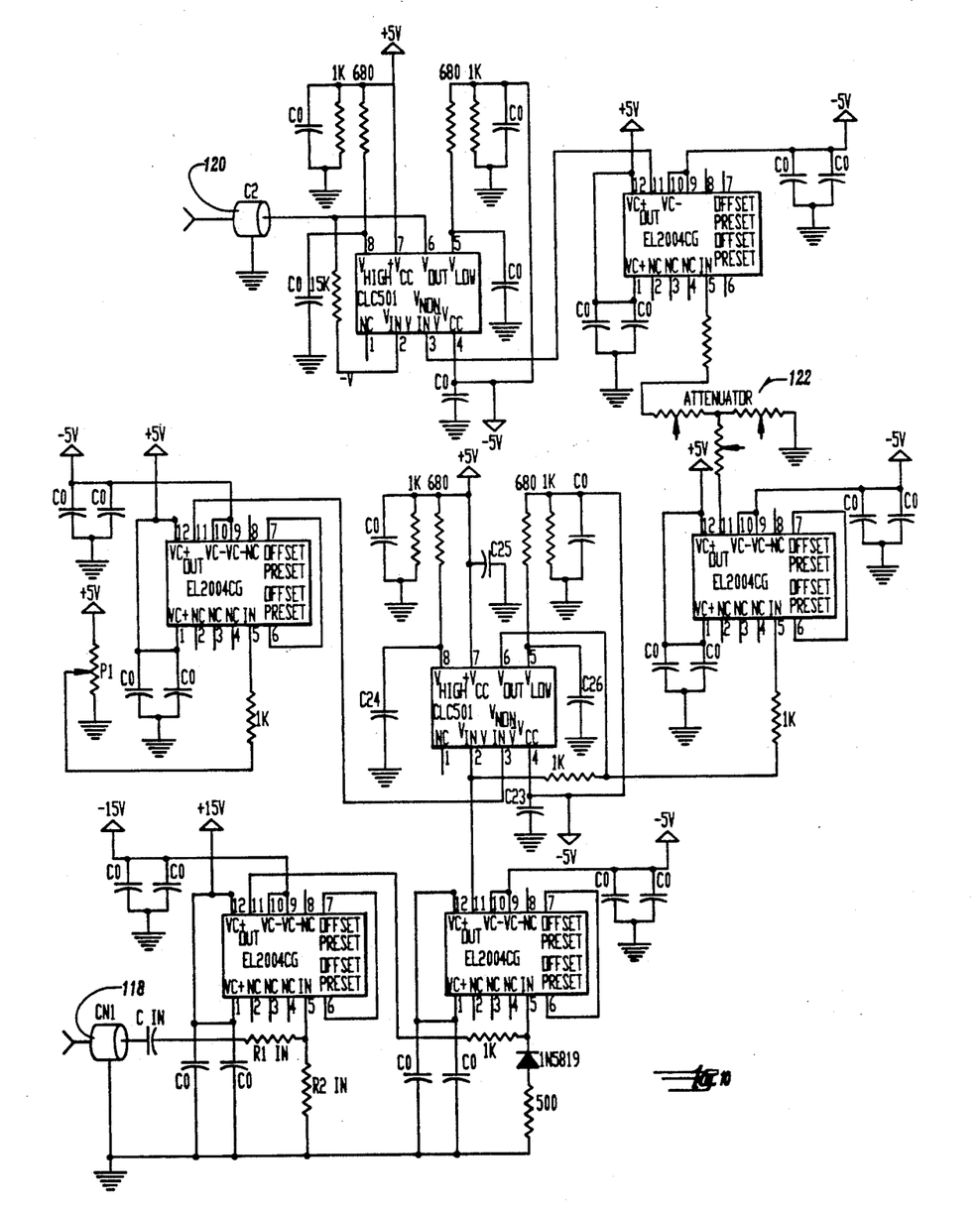
FIG. 10 is an electrical schematic of the receiver card of FIG. 3.

FIG. 10 is the electrical schematic for receiving circuit 32. Coaxial connector 118 is the connection from card 28 containing active switch 3, whereas coaxial connector 120 represents an output which can, in the preferred embodiment, be split into direct output 66 or a variable gain output 68.

Five EL2004CG devices are utilized, along with two CLC501 devices. An attenuator configuration 122 is utilized to vary the output gain of these amplifications.

It can therefore be seen how the invention meets at least all of its stated objectives. It will be appreciated that the present invention can take many forms or embodiments. The true essence and spirit of this invention are defined in the appended claims, and it is not intended that the embodiment of the invention presented herein should limit the scope of those claims.

What is claimed is:

1. An ultrasonic pulse/echo transmitting and receiving instrument comprising:
    an ultrasonic transducer means for transmitting and receiving ultrasonic mechanical acoustic pulses;
    electrical power supply means providing a source of electrical power;
    receiving circuit means for isolating and amplifying electrical signals representing return echoes of the acoustic pulses;
    timing and drive control circuit means for timing operations of the instrument and driving the transducer means to transmit periodic bursts of the acoustic pulses in a pulse mode;
    first switch means operatively connected between the electrical power supply means and the transducer means, controlled by the timing and drive control circuit means to send electrical power in an electrical pathway to the transducer means during a first time period;
    second switch means operatively positioned between the transducer means and ground, the second switch means providing a low impedance electrical pathway from the transducer means during a second time period;

third switch means operatively positioned between the transducer means and the receiving circuit means controlled by the timing and drive control circuit means to allow the receiving circuit means to receive the electrical signals representing return echoes of the acoustic pulses in an echo mode of the transducer means during a third time period; and the timing and drive circuit means including dual one shot triggering means for creating timing pulses in a first portion of the circuitry, and power MOSFET driver means for creating driving signals for the first, second, and third switch means of the instrument.

2. An ultrasonic pulse/echo transmitting and receiving instrument comprising:

an ultrasonic transducer means for transmitting and receiving ultrasonic mechanical acoustic pulses;

electrical power supply means providing a source of electrical power;

receiving circuit means for isolating and amplifying electrical signals representing return echoes of the acoustic pulses;

timing and drive control circuit means for timing operations of the instrument and driving the transducer means to transmit periodic bursts of the acoustic pulses in a pulse mode;

first switch means operatively connected between the electrical power supply means and the transducer means, controlled by the timing and drive control circuit means to send electrical power in an electrical pathway to the transducer means during a first time period, the first switch means including input from and adjustable direct current power supply, input from the timing and drive circuit means, a first MOSFET means between the input from the power supply and an outlet, and second MOSFET means between the input of the timing and drive means and the first MOSFET means, so that the operation of the second MOSFET means from the timing and drive means controls opening and closing of an electrical pathway between the power supply and the transducer means through the first MOSFET means;

second switch means operatively positioned between the transducer means and ground, the second switch means providing a low impedance electrical pathway from the transducer means during a second time period;

third switch means operatively positioned between the transducer means and the receiving circuit means controlled by timing and drive control circuit means to allow the receiving circuit means to receive the electrical signals representing return echoes of the acoustic pulses in an echo mode of the transducer means during a third time period.

3. The instrument of claim 2 wherein first and second diodes and a resistor are connected in series between the first MOSFET means and the input from the power supply.

4. An ultrasonic pulse/echo transmitting and receiving instrument comprising:

an ultrasonic transducer means for transmitting and receiving ultrasonic mechanical acoustic pulses;

electrical power supply means providing a source of electrical power;

receiving circuit means for isolating and amplifying electrical signals representing return echoes of the acoustic pulses;

timing and drive control circuit means for timing operations of the instrument and driving the transducer means to transmit periodic bursts of the acoustic pulses in a pulse mode;

first switch means operatively connected between the electrical power supply means and the transducer means, controlled by the timing and drive control circuit means to send electrical power in an electrical pathway to the transducer means during a first time period;

second switch means operatively positioned between the transducer means and ground, the second switch means providing a low impedance electrical pathway from the transducer means during a second time period; and third switch means operatively positioned between the transducer means and the receiving circuit means controlled by the timing and drive control circuit means to allow the receiving circuit means to receive the electrical signals representing return echoes of the acoustic pulses in an echo mode of the transducer means during a third time period, the third switch means including an input form the transducer means, an input from the timing and drive means, and an output to the receiving means, and including switching means to open and close an electrical pathway between the input from the transducer means, and the output to the receiving means, and further comprising a MOSFET and a buffer current amplifier in series between the input from the transducer means and the output to the receiving means, wherein the MOSFET has a voltage rating at least as large as the power supply means to protect the buffer current amplifier.

5. A drive for transmitting and receiving unipolar ultrasonic energy for sue in nondestructive evaluation comprising:

a housing to which components of the device can be installed;

first connection means on the housing to connect the device to an ultrasonic transducer means;

second connection means on the housing to connect the device to an electrical power source;

third connection means on the housing to connect the drive to a receiver amplifier means for providing an amplified received signal to an output;

power conversion means connected to the second connection means to provide one or more direct current voltages to the device;

control means for controlling timing and operation of the device according to parameters;

manually adjustable controls connected to the control means for adjusting the parameters related to the control means;

display means for displaying representations of one or more parameters;

first switch means for providing an electrical pathway for excitation voltage to the first connection means, the first switch means being controlled between non-conducting and conducting states by the control means and being conducting during a first time period to charge the transducer means;

second switch means for providing a low impedance electrical pathway to quickly discharge electrical charge from the transducer means, the second switch means being controlled by the control means to be conducting at a time after the first switch means is conducting and then non-conducting; and third switch means for providing an electrical pathway to the third connection means from the transducer means, the third switch means being controlled by the control means and being in a conducting state when ultrasonic energy is received through the third connection means, at a time substantially after the second switch means is non-conducting after being conducting.

6. The device of claim 5 wherein one of the direct current voltages used for an excitation voltage is a variable voltage generated according to a step function.

7. The device of claim 5 further comprising a housing means.

8. The device of claim 5 wherein the first, second and third switch means, receiving means, control means, and power converting means are contained on printed circuit boards installed in the housing.

9. The device of claim 8 wherein the printed circuit boards are constructed according to ground plane construction, include a ground plane, for fast pulse transition times and enhancement of noise immunity.

10. The device of claim 8 wherein the power conversion means and inputs from the control means are referenced to a separate ground other than the ground plane for eliminating ground loops which can degrade switching time for the first, second, and third switch means.

11. The device of claim 5 wherein first switching means includes the combination of five diodes and a band pass filter to decouple return echoes at first and second MOSFET devices.

12. The device of claim 5 wherein the second switching means includes a resistor and capacitor to decouple low frequency elements of return ultrasonic pulses to ground through a MOSFET gate drive circuitry.

13. The device of claim 5 wherein the third switch means comprises a MOSFET electrically connected to accept ultrasonic energy from said transducer means and a buffer current amplifier of limited input voltage range electrically connected to accept ultrasonic energy from said MOSFET.

14. The device of claim 5 wherein the first, second and third switching means are active switching means.

15. A method for transmitting and receiving unipolar ultrasonic nondestructive pulses comprising: cyclically triggering excitation voltage to a piezoelectric ultrasonic transducer; connecting by first active switch means the excitation voltage to the transducer at certain times and providing a low impedance transmission of electrical energy to the transducer to charge the transducer prior to creating a unipolar ultrasonic pulse; connecting by second active switch means a low impedance pathway to the transducer to discharge the transducer and propagate an ultrasonic mechanical acoustic pulse, and eliminating the low impedance pathway upon return echo of the ultrasonic pulse; and connecting by third active switch means the transducer to an amplifying and receiving means at a high impedance to communicate a return echo signal to the amplifying and receiving means.

16. The method of claim 15 wherein the excitation voltage is provided by a variable 0 to 1000 volts DC power supply.

17. The method of claim 15 further comprising the step of avoiding parasitic capacitive elements int he first, second, and third active switch means resulting in high impedance paths by decoupling the elements.

18. The method of claim 15 wherein the excitation voltage is created by a step function to produce ultrasonic pulses on the order of 10 nanoseconds or less at a magnitude over a range of 0 to 1000 volts.

19. The method of claim 15 wherein the first, second, and third active switch means utilize MOSFETs.

20. The method of claim 19 wherein further MOSFET devices are used to drive gate junctions of the MOSFETs of the first, second, and third active switch means.

21. The method of claim 15 wherein separate grounds are utilized for the excitation voltage means and for the first, second, and third active switch means, eliminating ground loop currents to increase signal band width.

* * * * *